US008318059B2

(12) United States Patent
Devlin et al.

(10) Patent No.: US 8,318,059 B2
(45) Date of Patent: Nov. 27, 2012

(54) STABILIZATION OF POLY(OXYALKYLENE) CONTAINING POLYMERIC MATERIALS

(75) Inventors: Brian Gerrard Devlin, Suwanee, GA (US); Arturo Norberto Medina, Duluth, GA (US); Karen Belinda Sentell, Alpharetta, GA (US); Stephen Raymond Perreault, Norcross, GA (US); Mireille Tena, Alpharetta, GA (US)

(73) Assignee: Novartis AG, Basel (CH)

( * ) Notice: Subject to any disclaimer, the term of this patent is extended or adjusted under 35 U.S.C. 154(b) by 398 days.

(21) Appl. No.: 12/456,409

(22) Filed: Jun. 16, 2009

(65) Prior Publication Data
US 2009/0263278 A1 Oct. 22, 2009

Related U.S. Application Data

(62) Division of application No. 10/723,680, filed on Nov. 25, 2003, now abandoned.

(60) Provisional application No. 60/429,719, filed on Nov. 27, 2002, provisional application No. 60/512,591, filed on Oct. 17, 2003.

(51) Int. Cl.
*B29C 71/00* (2006.01)

(52) U.S. Cl. ........... 264/2.6; 264/232; 264/340; 422/27; 422/28

(58) Field of Classification Search .................... 264/1.1, 264/2.6, 1.36, 1.38, 340, 232; 252/367.1; 422/26, 27, 28
See application file for complete search history.

(56) References Cited

U.S. PATENT DOCUMENTS

| | | | |
|---|---|---|---|
| 3,903,232 A | 9/1975 | Wood et al. .................... 264/157 |
| 4,886,866 A | 12/1989 | Braatz et al. .................... 528/59 |
| 4,894,486 A | 1/1990 | Neil, Jr. et al. ................. 568/702 |
| 4,910,277 A | 3/1990 | Bambury et al. ............. 526/260 |
| 4,919,151 A | 4/1990 | Grubbs et al. ................. 128/898 |
| 5,041,357 A | 8/1991 | Gersdorf et al. ............. 430/277 |
| 5,070,215 A | 12/1991 | Bambury et al. ............. 556/418 |
| 5,071,644 A | 12/1991 | Viegas |
| 5,077,033 A | 12/1991 | Viegas |
| 5,124,151 A | 6/1992 | Viegas |
| 5,143,731 A | 9/1992 | Viegas |
| 5,160,790 A | 11/1992 | Elton ............................ 428/412 |
| 5,175,229 A | 12/1992 | Braatz et al. .................... 528/48 |
| 5,179,186 A | 1/1993 | Muller et al. ................... 528/49 |
| 5,277,911 A | 1/1994 | Viegas |
| 5,290,585 A | 3/1994 | Elton ................................ 427/2 |
| 5,346,703 A | 9/1994 | Viegas |
| 5,367,001 A | 11/1994 | Itoh et al. ...................... 523/109 |
| 5,376,693 A | 12/1994 | Viegas |
| 5,393,858 A | 2/1995 | Meijs et al. ...................... 528/61 |
| 5,670,255 A * | 9/1997 | Temple et al. ................. 428/392 |
| 5,800,412 A | 9/1998 | Zhang |
| 5,847,023 A | 12/1998 | Viegas |
| 6,017,577 A | 1/2000 | Hostetler et al. ............. 427/2.12 |
| 6,103,267 A | 8/2000 | Mitchnick et al. ............ 424/489 |
| 6,346,272 B1 | 2/2002 | Viegas |
| 6,444,144 B1 | 9/2002 | Chung et al. ................... 252/407 |
| 6,451,871 B1 * | 9/2002 | Winterton et al. ............. 523/106 |
| 6,805,836 B2 | 10/2004 | Salamone |

FOREIGN PATENT DOCUMENTS

| | | |
|---|---|---|
| EP | 0 470 703 A1 | 2/1992 |
| EP | 0 593 284 A1 | 4/1994 |
| EP | 0 454 066 | 6/1996 |
| EP | 0 333 899 | 9/1996 |
| EP | 0 538 880 | 3/1999 |
| FR | 1500200 | 4/1966 |
| FR | 1500200 | 9/1967 |
| GB | 1177100 | 1/1970 |
| JP | 63-135483 | 6/1988 |
| JP | 63-135484 | 6/1988 |
| JP | 5-9472 | 1/1993 |
| JP | 5-156250 | 6/1993 |
| JP | 8280790 A | 10/1996 |
| JP | 10339854 A | 12/1998 |
| WO | WO 97/29166 | 8/1997 |
| WO | WO 01/14301 | 3/2001 |
| WO | WO 01/30910 | 5/2001 |
| WO | WO 02/13871 | 2/2002 |
| WO | WO 02/41044 | 5/2002 |

OTHER PUBLICATIONS

English Translation of JPO Notification of Reasons for Rejection, Dispatch No. 143920, Dispatch Date Mar. 2, 2010, for Japanese Patent Application No. 2004-554495.
Standard Search Report.
International Seach Report.
Reference D1 of the above mentioned Standard Search Report (XP-002254537).

\* cited by examiner

*Primary Examiner* — Mathieu D. Vargot
(74) *Attorney, Agent, or Firm* — Jian Zhou

(57) ABSTRACT

The present invention provides a method for producing a medical device, preferably an ophthalmic device, more preferably a contact lens, made of a stabilized poly(oxyalkylene)-containing polymeric material. The method of the invention comprises the steps of: curing, in a mold, a composition comprising (a) a prepolymer having at least one poly(oxyalkylene) unit, (b) a biocompatible organic multi-acid or biocompatible salt thereof in an amount sufficient to improve the stability of the poly(oxyalkylene)-containing polymer made from the composition, (c) optionally a photoinitiator or a thermal initiator, and (d) optionally one or more vinylic monomers, to form the medical device being less susceptible to oxidative degradation; and removing the medical device from the mold.

4 Claims, No Drawings

STABILIZATION OF POLY(OXYALKYLENE) CONTAINING POLYMERIC MATERIALS

This application is a division of U.S. patent application Ser. No. 10/723,680, filed Nov. 25, 2003, now abandoned, which claims the benefits under 35 USC §119 (e) of U.S. provisional application Nos. 60/429,719, filed Nov. 27, 2002 and 60/512,591, filed Oct. 17, 2003, both of which are incorporated by reference in their entireties.

The present invention relates to stabilization of poly(oxyalkylene)-containing polymeric materials. More specifically, the present invention relates to a method for stabilizing a poly(oxyalkylene)-containing polymeric material; a method for making a medical device, preferably an ophthalmic device, containing a stabilized poly(oxyalkylene)-containing polymeric material; a method for sterilizing a medical device having a core and/or a coating made of a poly(oxyalkylene)-containing polymeric material, wherein the method is characterized by having an improved stability of the poly(oxyalkylene)-containing polymeric material. In addition, the present invention relates to a stabilized poly(oxyalkylene)-containing polymeric material; a medical device comprising a core or a coating made of a stabilized poly(oxyalkylene)-containing polymeric material; and a solution for sterilizing and/or storing a medical device having a core or a coating made of a poly(oxyalkylene)-containing polymeric material, wherein the solution is capable of stabilizing the poly(oxyalkylene)-containing polymeric material.

BACKGROUND OF THE INVENTION

Because of the biocompatibility of poly(alkyleneglycols), also known as polyalkyl ethers or poly(alkylene oxide), poly(oxyalkylene)-containing polymers can find use in various fields, in particular in biomedical fields, such as, for example, carriers for drug-delivery, artificial tissues, dentifrices, contact lenses, intraocular lenses, and other biomedical devices. (For a recent review of applications see the ACS Symposium Series 680, "Poly(ethyleneglycol): Chemistry and Biological Applications", 1997, Harris and Zalipsky, eds.) However, poly(oxyalkylene)-containing polymers may be susceptible to degradation, in particular, oxidative degradation of its poly(oxyalkylene) chains under aerobic conditions. Oxidative degradation may cause changes in the properties of an article made from the poly(oxyalkylene)-containing polymers and limit the applications of poly(oxyalkylene)-containing polymers.

Susceptibility to oxidative degradation of a poly(oxyalkylene)-containing polymer can be effected by the method used in preparation and purification, post-manufacturing process (e.g., sterilization with autoclave, or the like), storage, and use. It is generally believed that, under aerobic conditions, a poly(oxyalkylene)-containing polymer may be degraded according to the mechanism of a free-radical chain reaction involving an oxidation step (see "Stability of the Polyoxyethylene Chain", Donbrow, Max. Surfactant Sci. Ser. (1987), 23 (Nonionic Surfactants), 1011-1072, and references contained therein). First, homolytic degradation of the alkylene glycol chain in a poly(oxyalkylene)-containing polymer is initiated photochemically, thermally, or chemically (e.g., by actinic radiation including UV radiation, ionizing radiation, or microwave, at elevated temperatures, or with free-radical initiators, etc.), producing an alkylene glycol radical. This radical undergoes spontaneous oxidation under aerobic conditions to form peroxides and hydroperoxides. The resulting peroxides and hydroperoxides may then undergo a variety of subsequent reactions to yield by-products such as formic acid, lower alcohols, and the like. For a contact lens made from a poly(oxyalkylene)-containing polymer, the poly(oxyalkylene) chain of the poly(oxyalkylene)-containing polymer may be susceptible to oxidative degradation, leading to formation of by-products such as formic acid and others. These by-products, especially formic acid which can have irritating effects, are not desirable, and thus need to be eliminated or minimized. Moreover, a medical device made from a poly(oxyalkylene)-containing polymer may have a shorter shelf life because of oxidative degradation of the poly(oxyalkylene)-containing polymer.

There have been attempts to stabilize poly(oxyalkylene)-containing materials used for medical devices by using antioxidants. For example, see U.S. Pat. Nos. 5,290,585, 5,160,790, 5,179,186, 5,367,001, 4,886,866 and 5,175,229, and EP 0333899B1. The antioxidants disclosed in those patents are hindered phenolic compounds, such as butylated hydroxytoluene, tris (3,5-di-t-butyl-4hydroxy benzyl) isocyanurate, 2,2'-methylenebis (4-methyl-6-t-lutyl phenol), 1,3,5-Trimethyl-2,4,6-tris (3,5-di-t-butyl-4-hydroxybenzyl) benzene, octadecyl 3,5, di-t-butyl-4hydroxyhydrocinnamate, 4,4 methylenebis (2,6-di-t-butylphenol), p,p-dioctyl diphenylamine, 1,1,3-tris-(2-methyl-4-hydroxy-5-t-butylphenyl) butane, Irganox (Ciba Geigy), and Santonox (Monsanto Corp.). However, there are some disadvantages associated with those antioxidants in the prior art for stabilizing poly(oxyalkylene)-containing materials. Those antioxidants may not be suitable for applications where the device is remain in contact with living tissues for long periods of times due to their cytotoxicity, or are water insoluble so that they can not be used in a water-base formulation for making the poly(oxyalkylene)-containing materials. Furthermore, those antioxidants may not be efficient in stabilizing poly(oxyalkylene)-containing materials and/or reducing the levels of by-products such as formic acid, in case where the poly(oxyalkylene)-containing materials are used to make contact lenses or other medical devices.

Accordingly, there is still a need for a method for stabilizing poly(oxyalkylene)-containing polymeric materials using a biocompatible material. Such stabilized poly(oxyalkylene)-containing polymeric materials can find particular use in making a medical device which are in contact with living cells or tissues.

SUMMARY OF THE INVENTION

One object of the invention is to provide a method for stabilizing a poly(oxyalkylene)-containing polymeric material using one or more biocompatible materials.

Another object of the invention is to provide a method for producing a stabilized poly(oxyalkylene)-containing polymeric material.

Still another object of the invention is to provide a method or a composition for making a medical device from a stabilized poly(oxyalkylene)-containing polymeric material.

A further object of the invention is to provide a stabilized poly(oxyalkylene)-containing polymeric material and a medical device made from a stabilized poly(oxyalkylene)-containing polymeric material.

A still further object of the invention is to provide a method for sterilizing a medical device made of a poly(oxyalkylene)-containing polymeric material while improving the stability of the poly(oxyalkylene)-containing polymeric material.

These and other objects of the invention are met by the various aspects of the invention described herein.

In accomplishing the foregoing, there is provided, in accordance with one aspect of the present invention, a stabilized poly(oxyalkylene)-containing polymeric material, which comprises: (a) a polymer network having at least one unit of formula (I)

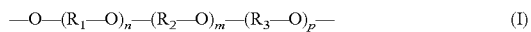

wherein $R_1$, $R_2$, and $R_3$, independently of one other, are each linear or branched $C_2$-$C_6$-alkylene, and n, m and p, independently of one another, are each a number from 0 to 100, wherein the sum of (n+m+p) is 5 to 1000, preferably 5 to 500, more preferably 5 to 200, even more preferably 8 to 120; and (b) a biocompatible organic multi-acid or biocompatible salt thereof present in an amount sufficient to improve the stability of the poly(oxyalkylene)-containing polymeric material, wherein the biocompatible organic multi-acid or biocompatible salt thereof is distributed within the polymeric material but not crosslinked to the polymer network. Preferably, the biocompatible organic multi-acid or biocompatible salt thereof is present in an amount effective to impart to the medical device a decreased susceptibility to oxidative degradation characterized by having at least an 1.5-fold reduction of the amount of detectable formic acid and optionally other degradation by-products.

In another aspect, the present invention provides a medical device comprising a poly(oxyalkylene)-containing polymeric material and a biocompatible organic multi-acid or biocompatible salt thereof present in an amount sufficient to improve the stability of the poly(oxyalkylene)-containing polymeric material, wherein the poly(oxyalkylene)-containing polymeric material has a polymer network having at least one unit of formula (I), and wherein the biocompatible organic multi-acid or biocompatible salt thereof is distributed within the poly(oxyalkylene)-containing polymeric material but not crosslinked to the polymer network. Preferably, the biocompatible organic multi-acid or biocompatible salt thereof is present in an amount effective to impart to the medical device a decreased susceptibility to oxidative degradation characterized by having at least an 1.5-fold reduction of the amount of detectable formic acid and optionally other degradation by-products.

In still another aspect, the present invention provides a method for producing a medical device, preferably an ophthalmic device, more preferably a contact lens, made of a stabilized poly(oxyalkylene)-containing polymeric material, the method comprising the steps of: (1) obtaining a polymerizable fluid composition comprising (a) a prepolymer having at least one poly(oxyalkylene) unit of formula (I) and ethylenically unsaturated groups, (b) a biocompatible organic multi-acid or biocompatible salt thereof, (c) optionally a photoinitiator or a thermal initiator, and (d) optionally one or more vinylic monomers; (2) introducing an amount of the polymerizable fluid composition in a mold for making the medical device; and (3) actinically or thermally polymerizing the polymerizable fluid composition in the mold to form the medical device having a polymer network having at least one unit of formula (I) and the biocompatible organic multi-acid or biocompatible salt thereof which is not crosslinked to the polymer network, wherein the biocompatible organic multi-acid or biocompatible salt thereof is present in an amount effective to improve the stability of the medical device so that the medical device has a decreased susceptibility to oxidative degradation characterized by having at least an 1.5-fold reduction of the amount of detectable formic acid and optionally other degradation by-products.

In a further aspect, the present invention provides a method for producing a medical device, preferably an ophthalmic device, more preferably a contact lens, made of a stabilized poly(oxyalkylene)-containing polymeric material, the method comprising the steps of: (1) introducing a reactive mixture into a mold for making the medical device by using a Reaction Injection Molding (RIM) process to form the medical device, wherein the reactive mixture comprises (a) at least one monomer or prepolymer having at least one poly(oxyalkylene) unit of formula (I) and functional groups which are amino, carboxy, hydroxyl or isocyanato groups and (b) at least one of an organic diamine, an organic polyamine, an organic diacid, an organic polyacid, an organic diol, an organic polyol, an organic diisocyanate, and organic polyisocyanate, provided that components (a) and (b) react with each other to form a polyurea and/or polyurethane network; (2) removing the medical device from the mold; and (3) impregnating the medical device with a biocompatible organic multi-acid or biocompatible salt thereof in an amount effective to improve the stability of the medical device so that the medical device has a decreased susceptibility to oxidative degradation characterized by having at least an 1.5-fold reduction of the amount of detectable formic acid and optionally other degradation by-products.

In another further aspect, the present invention provides a method for sterilizing a medical device which comprises a core material and/or a coating, wherein the core material and the coating, independently from each other, are made of a poly(oxyalkylene)-containing polymeric material, the method comprising: autoclaving the medical device in an aqueous solution containing a biocompatible organic multi-acid or biocompatible salt thereof in an amount sufficient to improve the stability of the poly(oxyalkylene)-containing polymeric material, so that the poly(oxyalkylene)-containing polymeric material has a decreased susceptibility to oxidative degradation characterized by having at least an 1.5-fold reduction of the amount of detectable formic acid and optionally other degradation by-products.

In still a further aspect, the present invention provides an aqueous solution for sterilizing and/or storing an ophthalmic device, wherein the ophthalmic device is made of a poly(oxyalkylene)-containing polymeric material, the aqueous solution having: a biocompatible organic multi-acid or biocompatible salt thereof in an amount sufficient to improve the stability of the poly(oxyalkylene)-containing polymeric material; an osmolarity of about 200 to 450 milli-osmole in 1000 ml (unit: mOsm/ml), wherein the aqueous solution is capable of improving the stability of the poly(oxyalkylene)-containing polymeric material, so that the poly(oxyalkylene)-containing polymeric material has a decreased susceptibility to oxidative degradation characterized by having at least an 1.5-fold reduction of the amount of detectable formic acid and optionally other degradation by-products.

These and other aspects of the invention will become apparent from the following description of the preferred embodiments. As would be obvious to one skilled in the art, many variations and modifications of the invention may be effected without departing from the spirit and scope of the novel concepts of the disclosure.

DETAILED DESCRIPTION OF THE PREFERRED EMBODIMENTS

Reference now will be made in detail to the embodiments of the invention. It will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention.

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. The nomenclature used herein and the laboratory procedures described below are those well known and commonly employed in the art.

An "article" refers to a medical device or a mold for making a medical device.

A "medical device", as used herein, refers to a device or a part thereof having one or more surfaces that contact tissue, blood, or other bodily fluids of patients in the course of their operation or utility. Exemplary medical devices include: (1) extracorporeal devices for use in surgery such as blood oxygenators, blood pumps, blood sensors, tubing used to carry blood and the like which contact blood which is then returned to the patient; (2) prostheses implanted in a human or animal body such as vascular grafts, stents, pacemaker leads, heart valves, and the like that are implanted in blood vessels or in the heart; (3) devices for temporary intravascular use such as catheters, guide wires, and the like which are placed into blood vessels or the heart for purposes of monitoring or repair; (4) artificial tissues such as artificial skin for burn patients; (5) dentifrices, dental moldings; (6) ophthalmic devices. In a preferred embodiment, medical devices are ophthalmic devices; and (7) cases or containers for storing ophthalmic devices or ophthalmic solutions.

An "ophthalmic device", as used herein, refers to a contact lens (hard or soft), an intraocular lens, a corneal onlay, other ophthalmic devices (e.g., stents, or the like) used on or about the eye or ocular vicinity.

"Biocompatible", as used herein, refers to a material or surface of a material, which may be in intimate contact with tissue, blood, or other bodily fluids of a patient for an extended period of time without significantly damaging the ocular environment and without significant user discomfort.

"Ophthalmically compatible", as used herein, refers to a material or surface of a material which may be in intimate contact with the ocular environment for an extended period of time without significantly damaging the ocular environment and without significant user discomfort. Thus, an ophthalmically compatible contact lens will not produce significant corneal swelling, will adequately move on the eye with blinking to promote adequate tear exchange, will not have substantial amounts of protein or lipid adsorption, and will not cause substantial wearer discomfort during the prescribed period of wear.

"Ocular environment", as used herein, refers to ocular fluids (e.g., tear fluid) and ocular tissue (e.g., the cornea) which may come into intimate contact with a contact lens used for vision correction, drug delivery, wound healing, eye color modification, or other ophthalmic applications.

A "monomer" means a low molecular weight compound that can be polymerized. Low molecular weight typically means average molecular weights less than 700 Daltons.

A "vinylic monomer", as used herein, refers to a low molecular weight compound that has an ethylenically unsaturated group and can be polymerized actinically or thermally. Low molecular weight typically means average molecular weights less than 700 Daltons. Exemplary ethylenically unsaturated groups include without limitation acryloyl, methacryloyl, allyl, vinyl, styrenyl, or other C=C containing groups.

A "hydrophilic vinylic monomer", as used herein, refers to a vinylic monomer which as a homopolymer typically yields a polymer that is water-soluble or can absorb at least 10 percent by weight water.

A "hydrophobic vinylic monomer", as used herein, refers to a vinylic monomer which as a homopolymer typically yields a polymer that is insoluble in water and can absorb less than 10 percent by weight water.

A "macromer" refers to a medium and high molecular weight compound or polymer 10 that contains functional groups capable of undergoing further polymerizing/crosslinking reactions. Medium and high molecular weight typically means average molecular weights greater than 700 Daltons. Preferably, a macromer contains ethylenically unsaturated groups and can be polymerized actinically or thermally.

A "polymer" means a material formed by polymerizing/crosslinking one or more monomers.

A "prepolymer" refers to a starting polymer which can be cured (e.g., crosslinked and/or polymerized) actinically or thermally or chemically to obtain a crosslinked and/or polymerized polymer having a molecular weight much higher than the starting polymer. Preferably, a prepolymer contains ethylenically unsaturated groups and can be polymerized actinically or thermally.

As used herein, "actinically" in reference to curing or polymerizing of a polymerizable composition or material means that the curing (e.g., crosslinked and/or polymerized) is performed by actinic irradiation, such as, for example, UV irradiation, ionized radiation (e.g. gamma ray or X-ray irradiation), and microwave irradiation.

A "photoinitiator" refers to a chemical that initiates radical crosslinking/polymerizing reaction by the use of light. Suitable photoinitiators include, without limitation, benzoin methyl ether, diethoxyacetophenone, a benzoylphosphine oxide, 1-hydroxycyclohexyl phenyl ketone, Darocure® types, and Irgacure® types, preferably Darocure® 1173, and Irgacure® 2959.

A "thermal initiator" refers to a chemical that initiates radical crosslinking/polymerizing reaction by the use of heat energy. Examples of suitable thermal initiators include, but are not limited to, 2,2'-azobis (2,4-dimethylpentanenitrile), 2,2'-azobis (2-methylpropanenitrile), 2,2'-azobis (2-methylbutanenitrile), peroxides such as benzoyl peroxide, and the like. Preferably, the thermal initiator is azobisisobutyronite (AIBN).

A "stabilized poly(oxyalkylene)-containing polymeric material" means that a poly(oxyalkylene)-containing polymeric material, which is prepared from a composition comprising a stabilizer and/or subjected to a sterilization treatment in a solution containing the stabilizer, is less susceptible to oxidative degradation (i.e., characterized by the amount of detectable formic acid and optionally other degradation by-products in a stabilized poly(oxyalkylene)-containing polymeric material being 80% or less, preferably 65% or less, more preferably 50% or less, of that detected in a non-stabilized poly(oxyalkylene)-containing polymeric material). A "non-stabilized poly(oxyalkylene)-containing polymeric material" means that a poly(oxyalkylene)-containing polymeric material, which is prepared from a composition without the stabilizer and/or subjected to a sterilization treatment in a solution without the stabilizer.

"Improve the stability of a poly(oxyalkylene)-containing polymeric material" means that the susceptibility to oxidative degradation of a poly(oxyalkylene)-containing polymeric material, which is prepared from a composition comprising a stabilizer and/or subjected to a sterilization treatment in a solution containing the stabilizer, is reduced (characterized by the amount of detectable formic acid and optionally other degradation by-products in a stabilized poly(oxyalkylene)-containing polymeric material being smaller than that detected in a non-stabilized corresponding poly(oxyalkylene)-containing polymeric material). The amount of detectable formic acid and optionally other degradation by-products derived from oxidative degradation of a poly(oxyalkylene)-containing polymeric material can be determined by any known suitable methods, such as, for example, ion-exchange chromatography described in Examples.

A "decreased susceptibility to oxidative degradation" in reference to a poly(oxyalkylene)-containing polymeric material or a medical device comprising a poly(oxyalkylene)-containing polymeric material means that its susceptibility to oxidative degradation is decreased by having a stabilizer therein. Typically, a decreased susceptibility to oxidative degradation of a poly(oxyalkylene)-containing polymeric material or a medical device comprising a poly(oxyalkylene)-containing polymeric material is characterized by having a stabilizer-induced reduction (preferably at least an 1.5-fold reduction, more preferably at least a 3-fold reduction, even more preferably at least a 5-fold reduction, most preferably at least a 10-fold reduction) of the amount of detectable formic acid and optionally other degradation by-products derived from oxidative degradation of the poly(oxyalkylene)-containing polymeric material. An "X-fold reduction of the amount of detectable formic acid and optionally other degradation by-products" means that, when comparing a stabilized poly(oxyalkylene)-containing polymeric material (or a stabilized medical device containing a stabilizer) with a corresponding non-stabilized poly(oxyalkylene)-containing polymeric material (or a non-stabilized medical device without a stabilizer), the amount of detectable formic acid and optionally other degradation by-products in the non-stabilized poly(oxyalkylene)-containing polymeric material (or the non-stabilized medical device) is at least X folds of the amount of detectable formic acid and optionally other degradation by-products in the stabilized poly(oxyalkylene)-containing polymeric material (or the stabilized medical device).

An "interpenetrating polymer network (IPN)" as used herein refers broadly to an intimate network of two or more polymers at least one of which is either synthesized and/or crosslinked in the presence of the other(s). Techniques for preparing IPN are known to one skilled in the art. For a general procedure, see U.S. Pat. Nos. 4,536,554, 4,983,702, 5,087,392, and 5,656,210, the contents of which are all incorporated herein by reference. The polymerization is generally carried out at temperatures ranging from about room temperature to about 145° C.

The present invention generally relates to a stabilized poly(oxyalkylene)-containing polymeric material and methods for making the same.

In one aspect, the present invention provides a stabilized poly(oxyalkylene)-containing polymeric material. A stabilized poly(oxyalkylene)-containing polymeric material of the invention comprises: (a) a polymer network having at least one unit of formula (I)

$$-O-(R_1-O)_n-(R_2-O)_m-(R_3-O)_p- \quad (I)$$

wherein $R_1$, $R_2$, and $R_3$, independently of one other, are each linear or branched $C_2$-$C_6$-alkylene, and n, m and p, independently of one another, are each a number from 0 to 100, wherein the sum of (n+m+p) is 5 to 1000, preferably 5 to 500, more preferably 5 to 200, even more preferably 8 to 120; and (b) a biocompatible organic multi-acid or biocompatible salt thereof present in an amount sufficient to improve the stability of the poly(oxyalkylene)-containing polymeric material, which is distributed within the polymeric material but not crosslinked to the polymer network.

In accordance with the present invention, a poly(oxyalkylene)-containing polymeric material can be any polymer which is a reaction product of a mixture including a poly(oxyalkylene) polymer with functional groups (e.g., amino, hydroxyl, acid, or isocyanato groups) and at least a chemical with functional groups (e.g., amino, hydroxyl, isocyanato, or acid groups) which are co-reactive with the functional groups of poly(oxyalkylene) polymer. Examples of such polymer include without limitation: (1) a polyester obtained by esterification of the terminal diols of a hydroxy terminated (diols) poly(oxyalkylene)-containing polymer with organic monoacids or diacids such as, for example, glutaric or adipic acids; (2) a polyamide obtained by reacting an amine terminated poly(oxyalkylene)-containing polymer with organic monoacids or diacids acids such as, for example, glutaric or adipic acids; (3) a polyurethane which is the copolymerization product of a mixture comprising one or more hydroxyl (or isocyanate)-terminated poly(oxyalkylene)-containing polymer and one or more organic di- or polyisocyanates (or diols or polyols); (4) a polyurea which is the copolymerization product of a mixture comprising one or more amine (or isocyanate)-terminated poly(oxyalkylene)-containing polymer and one or more di- or multi-isocyanates (or diamines or polyamines); and a polyurea/polyurethane which is the copolymerization product of a mixture comprising one or more amine or hydroxy-terminated poly(oxyalkylene)-containing polymer, one or more di- or multi-isocyanates and one or more organic di- or polyamines (or di- or polyols). The above examples have been given as a means of illustrating the aspects of the invention and are not limiting in any way. It should be understood that a poly(oxyalkylene)-containing polymeric material can also contain one or more silicone and/or fluorine atoms.

In accordance with the present invention, a poly(oxyalkylene)-containing polymeric material can also be an interpenetrating or semi-interpenetrating polymer network. Exemplary interpenetrating polymer networks are interpenetrating polyurea/polyacrylic networks disclosed in EP 0735097 B1. Such interpenetrating polyurea/polyacrylic networks are formed by polymerizing a reactive mixture comprising: (a) at least one amine-terminated poly(alkylene glycol); (b) an organic di- or polyisocyanate which reacts with (a) to form a polyurea network; (c) an acrylic ester; (d) a free radical initiator to polymerize (c) to form a polyacrylic network; and (e) a triamine to crosslink (a).

Exemplary poly(alkylene glycol)s include, but are not limited to, a poly(ethylene glycol), a poly(1-propylene glycol), a poly(2-propylene glycol), a poly(ethylene glycol)/poly(propylene glycol) block polymer, a poly(ethylene glycol)/poly(propylene glycol)/poly(butylene glycol) block polymer, a polytetrahydrofuran, a poloxamer, and the like.

In accordance with the present invention, a stabilized poly(oxyalkylene)-containing polymeric material has a decreased susceptibility to oxidative degradation, characterized by having preferably at least an 1.5-fold reduction of, more preferably at least a 3-fold reduction, even more preferably at least a 5-fold reduction of, most preferably at least 10-fold reduction of the amount of detectable formic acid and optionally other degradation by-products.

Any known suitable organic multi-acids or biocompatible salts thereof, which are water-soluble, non-toxic, biocompatible, and capable of stabilizing poly(oxyalkylene) chains in the presence of UV light or free radical sources or at high temperatures. Exemplary organic multi-acids suitable for the present invention include, but are not limited to, hydroxy diacids, hydroxy multi-acids, amino acids, and the like. Preferably, an organic multi-acid of the present invention is an α-oxo-multi-acid, such as, for example, citric acid, 2-ketoglutaric acid, or malic acid. More preferably, an organic multi-acid is citric or malic acid. Biocompatible (preferably ophthalmically compatible) salts of organic multi-acids suitable for the present invention include sodium, potassium, and ammonium salts.

As used herein, an "alpha-oxo-multiacid" refers to an acid which has a plurality (two or more) of carboxyl groups and at least one carbon atom which is simultaneously substituted by a carboxyl group and an oxygen atom, i.e., O—C—COOR, wherein the oxygen could be a carbonyl, a hydroxy, an esterified hydroxy, an ether, or the like, and wherein the oxygen is on the carbon which is alpha to the carboxyl group.

In accordance with the present invention, a biocompatible organic multi-acid or biocompatible salt thereof can be introduced into a stabilized poly(oxyalkylene)-containing polymeric material either by adding it into a pre-polymerization composition for making the poly(oxyalkylene)-containing polymeric material and/or by immersing a poly(oxyalkylene)-containing polymeric material in a solution containing the biocompatible organic multi-acid or biocompatible salt thereof (i.e., impregnation of the poly(oxyalkylene)-containing polymeric material with the biocompatible organic multi-acid or biocompatible salt thereof).

The concentration of a biocompatible organic multi-acid or biocompatible salt thereof in a pre-polymerization composition for making a stabilized poly(oxyalkylene)-containing polymeric material or in a solution for impregnation of the poly(oxyalkylene)-containing polymeric material with the biocompatible organic multi-acid or biocompatible salt thereof is preferably from 0.001 millimolar to the solubility limit of a particular biocompatible organic multi-acid or biocompatible salt thereof, more preferentially from 10 to 300 millimolar. It is understood that the weight percentages will change based on the molecular weight of the acid employed.

In a preferred embodiment, a stabilized poly(oxyalkylene)-containing polymeric material of the invention is a copolymerization product of a composition comprising:
(a) a prepolymer containing ethylenically unsaturated groups and at least one unit of formula (I)

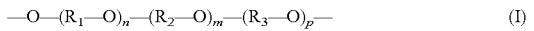

wherein $R_1$, $R_2$, and $R_3$, independently of one other, are each linear or branched $C_2$-$C_4$-alkylene, and n, m and p, independently of one another, are each a number from 0 to 100, wherein the sum of (n+m+p) is 5 to 1000, preferably 5 to 500, more preferably 5 to 200, even more preferably 8 to 120;
(b) a water-soluble and biocompatible organic multi-acid or biocompatible salt thereof in an amount sufficient to improve the stability of the poly(oxyalkylene)-containing polymeric material made from the composition;
(c) optionally a photoinitiator or a thermal initiator; and
(d) optionally one or more vinylic monomers.

In another preferred embodiment, a stabilized poly(oxyalkylene)-containing polymeric material of the invention is a poly(oxyalkylene)-containing polymeric material impregnated with a biocompatible organic multi-acid or biocompatible salt thereof in an amount sufficient to improve the stability of the poly(oxyalkylene)-containing polymeric material, wherein the poly(oxyalkylene)-containing polymeric material is a copolymerization product of a composition comprising:
(a) a prepolymer containing ethylenically unsaturated groups and at least one unit of formula (I)

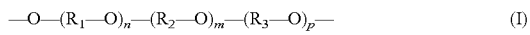

wherein $R_1$, $R_2$, and $R_3$, independently of one other, are each linear or branched $C_2$-$C_4$-alkylene, and n, m and p, independently of one another, are each a number from 0 to 100, wherein the sum of (n+m+p) is 5 to 1000, preferably 5 to 500, more preferably 5 to 200, even more preferably 8 to 120;
(b) optionally a photoinitiator or a thermal initiator; and
(c) optionally one or more vinylic monomers.

Impregnation of a poly(oxyalkylene)-containing polymeric material can be performed according to any known suitable methods, for example, such as immersing the poly(oxyalkylene)-containing polymeric material in a solution containing a biocompatible organic multi-acid or biocompatible salt thereof.

A prepolymer having at least one unit of formula (I) and ethylenically unsaturated groups can be prepared according to any methods known to a person skilled in the art. For example, ethylenically unsaturated groups, such as, for example, acryloyl, methacryloyl, allyl, vinyl, styrenyl, or other C═C containing groups, could be covalently attached to the poly(alkylene glycol) moiety according to any method known to a person skilled in the art.

One example of such prepolymer is a crosslinkable polyurea polymer described in U.S. Pat. No. 6,479,587, herein incorporated by reference in its entirety. Such crosslinkable polyurea polymer can be prepared by introducing ethylenically unsaturated groups into a polyurea which is the copolymerization product of a reaction mixture including at least one amine-terminated poly(alkylene glycol) and an organic di- or polyisocyanate.

A further example is a crosslinkable polyurethane described in U.S. patent application Ser. No. 10/640,294 filed on Aug. 13, 2003 (herein incorporated by reference in its entirety). Such crosslinkable polyurethane polymer can be prepared by introducing ethylenically unsaturated groups into an isocyanate-capped polyurethane which is the copolymerization product of a reaction mixture including at least one hydroxy-terminated poly(alkylene glycol) and an organic di- or polyisocyanate.

The vinylic monomer which may be additionally used for photo-crosslinking in accordance with the invention may be hydrophilic, hydrophobic or may be a mixture of a hydrophobic and a hydrophilic vinylic monomer. Suitable vinylic monomers include especially those normally used for the manufacture of contact lenses.

It is preferable to use a hydrophobic vinylic monomer, or a mixture of a hydrophobic vinylic monomer with a hydrophilic vinylic monomer, whereby this mixture contains at least 50 percent by weight of a hydrophobic vinyl monomer. In this way, the mechanical properties of the polymer may be improved without the water content dropping substantially. Both conventional hydrophobic vinylic monomers and conventional hydrophilic vinylic monomers are suitable for copolymerization with the radiation-curable prepolymers according to the invention.

Suitable hydrophobic vinylic monomers include, without limitation, $C_1$-$C_{18}$-alkylacrylates and -methacrylates, $C_3$-$C_{18}$ alkylacrylamides and -methacrylamides, acrylonitrile, methacrylonitrile, vinyl-$C_1$-$C_{18}$-alkanoates, $C_2$-$C_{18}$-alkenes, $C_2$-$C_{18}$-halo-alkenes, styrene, $C_1$-$C_6$-alkylstyrene, vinylalkylethers in which the alkyl moiety has 1 to 6 carbon atoms, $C_2$-$C_{10}$-perfluoralkyl-acrylates and -methacrylates or correspondingly partially fluorinated acrylates and methacrylates, $C_3$-$C_{12}$-perfluoralkyl-ethyl-thiocarbonylaminoethyl-acrylates and -methacrylates, acryloxy and methacryloxy-alkylsiloxanes, N-vinylcarbazole, $C_1$-$C_{12}$-alkylesters of maleic acid, fumaric acid, itaconic acid, mesaconic acid and the like. Preference is given e.g. to $C_1$-$C_4$-alkylesters of vinylically unsaturated carboxylic acids with 3 to 5 carbon atoms or vinylesters of carboxylic acids with up to 5 carbon atoms.

Examples of suitable hydrophobic vinylic monomers include methylacrylate, ethyl-acrylate, propylacrylate, isopropylacrylate, cyclohexylacrylate, 2-ethylhexylacrylate, methylmethacrylate, ethylmethacrylate, propylmethacrylate, vinyl acetate, vinyl propionate, vinyl butyrate, vinyl valerate, styrene, chloroprene, vinyl chloride, vinylidene chloride, acrylonitrile, 1-butene, butadiene, methacrylonitrile, vinyl toluene, vinyl ethyl ether, perfluorohexylethyl-thio-carbonylaminoethyl-methacrylate, isobornyl methacrylate, trifluoroethyl methacrylate, hexafluoro-isopropyl methacrylate, hexafluorobutyl methacrylate, tris-trimethylsilyloxy-silylpropyl methacrylate, 3-methacryloxypropyl-pentamethyldisiloxane and bis(methacryloxypropyl)-tetramethyl-disiloxane.

Suitable hydrophilic vinylic monomers include, without limitation, hydroxy-substituted lower alkylacrylates and -methacrylates, acrylamide, methacrylamide, lower alkyl-acrylamides and -methacrylamides, ethoxylated acrylates and methacrylates, hydroxy-substituted lower alkyl-acrylamides and -methacrylamides, hydroxy-substituted lower alkylvinyl-ethers, sodium ethylene sulphonate, sodium styrene sulphonate, 2-acrylamido-2-methyl-propane-sulphonic acid, N-vinyl pyrrole, N-vinyl succinimide, N-vinyl pyrrolidone, 2- or 4-vinyl pyridine, acrylic acid, methacrylic acid, amino- (whereby the term "amino" also includes quaternary ammonium), mono-lower-alkylamino- or di-lower-alkylamino-lower-alkyl-acrylates and -methacrylates, allyl alcohol and the like. Preference is given e.g. to hydroxy-substituted $C_2$-$C_4$-alkyl(meth)acrylates, five- to seven-membered N-vinyl-lactams, N,N-di-$C_1$-$C_4$-alkyl-methacrylamides and vinylically unsaturated carboxylic acids with a total of 3 to 5 carbon atoms.

Examples of suitable hydrophilic vinylic monomers include hydroxyethyl methacrylate, hydroxyethyl acrylate, acrylamide, methacrylamide, dimethylacrylamide, allyl alcohol, vinyl pyridine, vinyl pyrrolidone, glycerol methacrylate, N-(1,1-dimethyl-3-oxobutyl)acrylamide, and the like.

Preferred hydrophobic vinylic monomers are methyl methacrylate and vinyl acetate. Preferred hydrophilic vinylic monomers are 2-hydroxyethyl methacrylate, N-vinyl pyrrolidone and acrylamide.

A photo-initiator or thermal initiator is advantageously added to a composition of the invention. The amount of photo-initiator may be selected from a wide range, whereby an amount of up to 0.05 g/g polymer and especially up to 0.003 g/g polymer has proved favorable.

A composition of the invention can further comprise a color additive which is capable of creating a light colored visibility tint. Such tint can facilitate the handling of ophthalmic lenses. Any known suitable color additives can be used. Preferably, copper phthalocyanin is used as a color additive which is capable of creating a light blue or light green or other light color visibility tint.

A composition of the invention can optionally comprise other additives, such as, for example, a crosslinking agent, an antimicrobial agents, and/or the like.

Preferably, a composition of the invention is a water-based composition.

Optionally a solvent may be present in a composition of the invention. Any known suitable solvents can be used. Exemplary solvents include, but are not limited to, alcohols, such as lower alkanols, for example ethanol or methanol, and furthermore carboxylic acid amides, such as dimethylformamide, dipolar aprotic solvents, such as dimethyl sulfoxide or methyl ethyl ketone, ketones, for example acteone or cyclohexanone, hydrocarbons, for example toluene, ethers, for example THF, dimethoxyethane or dioxane, and halogenated hydrocarbons, for example trichloroethane, and also mixtures of suitable solvents, for example mixtures of water with an alcohol, for example a water/ethanol or a water/methanol mixture. A person skilled in the art will know how to select a solvent.

A composition of the invention for preparing a stabilized poly(oxyalkylene)-containing polymeric material can find use in making a medical device, preferably an ophthalmic device, more preferably a contact lens.

In another aspect, the present invention provides a method for producing a medical device, preferably an ophthalmic device, more preferably a contact lens, made of a stabilized poly(oxyalkylene)-containing polymeric material, the method comprising the steps of: (1) obtaining a polymerizable fluid composition comprising (a) a prepolymer having at least one poly(oxyalkylene) unit of formula (I) and ethylenically unsaturated groups, (b) a biocompatible organic multi-acid or biocompatible salt thereof, (c) optionally a photoinitiator or a thermal initiator, and (d) optionally one or more vinylic monomers; (2) introducing an amount of the polymerizable fluid composition in a mold for making the medical device; and (3) actinically or thermally polymerizing the polymerizable fluid composition in the mold to form the medical device having a polymer network having at least one unit of formula (I) and the biocompatible organic multi-acid or biocompatible salt thereof which is not crosslinked to the polymer network, wherein the biocompatible organic multi-acid or biocompatible salt thereof is present in an amount effective to improve the stability of the medical device so that the medical device has a decreased susceptibility to oxidative degradation characterized by having at least an 1.5-fold reduction of the amount of detectable formic acid and optionally other degradation by-products.

The polymerizable fluid composition can be introduced into a mold by methods known per se, especially conventional dispensing, e.g. dropwise addition in a desired quantity.

Appropriate disposable molds are made, for example, from polypropylene. Suitable materials for re-usable mounds are e.g. quartz, sapphire glass or metals.

If the molded articles to be produced are contact lenses, these may be produced in a manner known per se, e.g. in a conventional "spin-casting mold", as described for example in U.S. Pat. No. 3,408,429, or by the so-called full mold process in a static form, as described e.g. in U.S. Pat. Nos. 4,347,198, 5,508,317, 5,583,463, 5,789,464, and 5,849,810.

Crosslinking/polymerizing of the composition may be initiated in the mold actinically (e.g. by means of actinic radiation, such as UV irradiation, gamma or X-ray irradiation) or thermally.

Opening of the mold so that the molded article can be removed from the mold may take place in a manner known per se.

If the molded article produced according to the invention is a contact lens which is produced solvent-free from an already purified crosslinkable prepolymer in the absence of vinylic monomers according to the invention, then after removal of the molded article, it is not normally necessary to follow up with purification steps such as extraction. This is because the prepolymers employed do not contain any undesired constituents of low molecular weight; consequently, the crosslinked product is also free or substantially free from such constituents and subsequent extraction can be dispensed with. Accordingly, the contact lens can be directly transformed in the usual way, by hydration, into a ready-to-use contact lens. Appropriate embodiments of hydration are known to the person skilled in the art, whereby ready-to-use contact lenses with very varied water content may be obtained. The contact lens (in particular, a hydrogel contact lens) is expanded, for example, in water, in an aqueous salt solution, especially an aqueous salt solution having an osmolarity of about 200 to 450 milli-osmole in 1000 ml (unit: mOsm/ml), preferably about 250 to 350 mOsm/l and especially about 300 mOsm/l, or in a mixture of water or an aqueous salt solution with a physiologically compatible polar organic solvent, e.g. glycerol. Preference is given to expansions of the article in water or in aqueous salt solutions.

The aqueous salt solutions used for hydration are advantageously solutions of physiologically compatible salts, such as buffer salts conventionally used in the field of contact lens care, e.g. phosphate salts, or isotonizing agents conventionally used in the field of contact lens care, such as in particular alkali halides, e.g. sodium chloride, or solutions of mixtures thereof. One example of an especially suitable salt solution is an artificial, preferably buffered lachrymal fluid, which is adapted to natural lachrymal fluid as regards pH value and osmolarity, e.g. an unbuffered or preferably buffered common salt solution, for example buffered by phosphate buffer, whose osmolarity and pH value correspond to the osmolarity and pH value of human lachrymal fluid.

The aqueous salt solutions used for hydration preferably contain biocompatible organic multi-acids or biocompatible salts thereof in an amount sufficient to improve the stability of the poly(oxyalkylene)-containing polymer made from the composition.

The above-defined hydration fluids are preferably at least substantially free from undesired constituents. This is most preferably pure water or an artificial lachrymal fluid as described above.

If the molded article produced according to the invention is a contact lens which is produced from an aqueous solution of an already purified crosslinkable prepolymer in the absence of vinylic monomers according to the invention, then the crosslinked product is likely not to contain any impurities. It is therefore not necessary to carry out subsequent extraction. Since crosslinking is carried out in an essentially aqueous solution, it is additionally unnecessary to carry out subsequent hydration. The contact lenses obtained by this process are therefore notable, according to an advantageous embodiment, for the fact that they are suitable for their intended usage without extraction. By intended usage is understood, in this context, that the contact lenses can be used in the human eye.

The contact lenses obtained according to the invention have a low susceptibility to oxidative degradation, characterized by having a reduced amount of formic acid and/or other degradation by-products detected in the contact lenses. They may have a longer shelf life. Moreover, because of reduction in the formation of formic acid, the contact lenses obtained according to the invention may not cause irritation to the eyes of a wearer.

Of course, all the above-mentioned advantages apply not only to contact lenses, but also to other molded articles according to the invention, for example, an implantable medical device obtained according to the invention. The total of the different advantageous aspects during production of the molded articles according to the invention leads to the suitability of the molded articles in particular as mass-produced articles, for example, as contact lenses which are for daily use and/or for weekly use.

In still another aspect, the present invention provides a method for producing a medical device, preferably an ophthalmic device, more preferably a contact lens, made of a stabilized poly(oxyalkylene)-containing polymeric material, the method comprising the steps of: (1) introducing a reactive mixture into a mold for making the medical device by using a Reaction Injection Molding (RIM) process to form the medical device, wherein the reactive mixture comprises (a) a monomer or prepolymer having at least one poly(oxyalkylene) unit of formula (I) and functional groups which are amino, carboxy, hydroxyl or isocyanato groups and (b) an organic diamine, an organic polyamine, an organic diacid, an organic polyacid, an organic diol, an organic polyol, an organic diisocyante, or organic polyisocyanate, provided that components (a) and (b) react with each other to form a polyurea and/or polyurethane network; (2) removing the medical device from the mold; and (3) impregnating the medical device with a biocompatible organic multi-acid or biocompatible salt thereof in an amount effective to improve the stability of the medical device so that the medical device has a decreased susceptibility to oxidative degradation characterized by having at least an 1.5-fold reduction of the amount of detectable formic acid and optionally other degradation by-products.

The RIM process is a known molding process wherein two or more streams of monomers react in the mold to form a polymer; and is well described by L. T. Manzione in The Encyclopedia of Polymer Science and Engineering; 2nd Edition Vol 14, pg. 72, herein incorporated by reference in its entirety.

In a preferred embodiment, the reactive mixture can further comprise one or more prepolymers having ethylenically unsaturated groups or one or more vinylic monomers to form a different polymer network which interpenetrate with the polyurea and/or polyurethane network.

In a further aspect, the present invention provides a medical device comprising a poly(oxyalkylene)-containing polymeric material and a biocompatible organic multi-acid or biocompatible salt thereof present in an amount sufficient to improve the stability of the poly(oxyalkylene)-containing polymeric material, wherein the poly(oxyalkylene)-containing polymeric material has a polymer network having at least one unit of formula (I)

$$-O-(R_1-O)_n-(R_2-O)_m-(R_3-O)_p- \quad (I)$$

in which $R_1$, $R_2$, and $R_3$, independently of one other, are each linear or branched $C_2$-$C_6$-alkylene, and n, m and p, independently of one another, are each a number from 0 to 100, wherein the sum of (n+m+p) is 5 to 1000, preferably 5 to 500, more preferably 5 to 200, even more preferably 8 to 120, and wherein the biocompatible organic multi-acid or biocompatible salt thereof is distributed within the poly(oxyalkylene)-containing polymeric material but not crosslinked to the polymer network. The biocompatible organic multi-acid or biocompatible salt thereof is present in an amount effective to improve the stability of the medical device so that the medical device has a decreased susceptibility to oxidative degradation characterized by having preferably at least an 1.5-fold reduction of, more preferably at least a 3-fold reduction of, even more preferably at least a 5-fold reduction, most preferably at least a 10-fold reduction of the amount of detectable formic acid and optionally other degradation by-products.

In a preferred embodiment, the medical device of the invention is a polymerization product of a composition comprising (a) a prepolymer containing ethylenically unsaturated groups and at least one poly(oxyalkylene) unit of formula (I); (b) a water-soluble and biocompatible organic multi-acid or biocompatible salt thereof in an amount sufficient to improve the stability of a poly(oxyalkylene)-containing polymeric material made from the composition; (c) optionally a photoinitiator or a thermal initiator; and (d) optionally one or more vinylic monomers.

In another preferred embodiment, the biocompatible organic multi-acid or biocompatible salt thereof is impregnated within the poly(oxyalkylene)-containing polymeric material, wherein the poly(oxyalkylene)-containing polymeric material is a polymerization product of a reactive mixture comprising (a) at least one monomer or prepolymer having at least one poly(oxyalkylene) unit of formula (I) and functional groups which are amino, carboxy, hydroxyl or isocyanato groups, and (b) at least one of an organic diamine, an organic polyamine, an organic diacid, an organic polyacid, an organic diol, an organic polyol, an organic diisocyante, and organic polyisocyanate, provided that components (a) and (b) react with each other to form a polyurea and/or polyurethane network. More preferably, the reactive mixture further comprises one or more vinylic monomers or prepolymer with ethylenically unsaturated groups. Those monomers or prepolymers can form upon actinical irradiation a different polymer network which interpenetrates the polyurea and/or polyurethane network.

In another further aspect, the present invention provides a method for sterilizing a medical device which comprises a core material and/or a coating, wherein the core material and the coating, independently of each other, are made of a poly(oxyalkylene)-containing polymeric material, the method comprising: autoclaving the medical device in a solution containing a water-soluble and biocompatible organic multi-acid or biocompatible salt thereof in an amount sufficient to improve the stability of the poly(oxyalkylene)-containing polymeric material, so that the poly(oxyalkylene)-containing polymeric material has a decreased susceptibility to oxidative degradation characterized by having at least an 1.5-fold reduction of the amount of detectable formic acid and optionally other degradation by-products.

A medical device can be coated with a poly(oxyalkylene)-containing material according to any methods known to a person skilled in the art. Exemplary coating techniques include, but are not limited to, dip coating, spraying coating, painting, knife-coating, and printing.

In still a further aspect, the present invention provides an aqueous solution for sterilizing and/or storing an ophthalmic device, wherein the ophthalmic device is made of a poly(oxyalkylene)-containing polymeric material, the aqueous solution having: a biocompatible organic multi-acid or biocompatible salt thereof in an amount sufficient to improve the stability of the poly(oxyalkylene)-containing polymeric material; an osmolarity of about 200 to 450 milli-osmole in 1000 ml (unit: mOsm/ml), wherein the aqueous solution is capable of improving the stability of the poly(oxyalkylene)-containing polymeric material, so that the poly(oxyalkylene)-containing polymeric material has a reduced susceptibility to oxidative degradation characterized by having at least an 1.5-fold reduction of the amount of detectable formic acid and optionally other degradation by-products.

An aqueous solution of the invention has an osmolarity of, preferably from about 250 to 350 mOsm/l, more preferably about 300 mOsm/l. An aqueous solution of the invention can comprise physiologically compatible salts, such as buffer salts conventionally used in the field of contact lens care, e.g. phosphate salts, or isotonizing agents conventionally used in the field of contact lens care, such as in particular alkali halides, e.g. sodium chloride. An aqueous solution of the invention can further comprise a physiologically compatible polar organic solvent, e.g. glycerol.

The previous disclosure will enable one having ordinary skill in the art to practice the invention. In order to better enable the reader to understand specific embodiments and the advantages thereof, reference to the following non-limiting examples is suggested. However, the following examples should not be read to limit the scope of the invention.

Example 1

68.63 g of Jeffamine XTJ-501, 16.04 g of Jeffamine XTJ-502 (both from Huntsman Corporation), and 2.14 g of diethylene triamine (Aldrich Chemicals) were weighed in a jacketed 1-L reactor. 370 g of tetrahydrofuran (Aldrich) and 200 g of deionized water were added to the reactor and the contents were stirred to be dissolved. A sample was taken for titration (0.332 mAeq/g vs. 0.335 by theory). The reactor was then chilled to 0° C. with stirring under nitrogen. 21.74 g of isophorone diisocyanate (Aldrich Chemicals, used as received) was then dissolved in 35 g of THF and added dropwise over 45 minutes. The solution was stirred at temperature for one hour, and then a sample was withdrawn and titrated (0.033 mAeq/g vs. 0.035 theory). 3.5 g of cyclohexylisocyanate (Aldrich Chemicals, used as received) was then added in one portion, and the reactor was stirred at 0° C. for one hour. The product was then decanted to a 2-L flask, and the reactor was chased with 400 mL of water. The combined products were concentrated on a rotary evaporator at 53° C./80 mBar ultimate vacuum to yield a solution essentially free of tetrahydrofuran. This solution was then ultrafiltered with 20 L of water using a 3-kilodalton membrane. The resulting purified solution was then concentrated to 50% solids on a rotary evaporator.

Example 2

70 g of Poly(ethylene glycol) with a molecular weight of approximately 2000, available from Aldrich Chemicals, was dissolved in 70 g of water.

Example 3

2.00 g of Sodium Ascorbate (Aldrich) was dissolved in 20 g with water. pH was adjusted to 6.92 by addition of 100 µL of 10% Ascorbic acid in water (Aldrich Chemicals). 1.00 g of Irgacure®-2959 (2-Hydroxy-4'-(2-hydroxyethyl)-2-methylpropiophenone, available from Ciba Specialty Chemicals) was mixed with 8.83 g of the ascorbate buffer, and then diluted to 100 g with water. The mixture was dissolved with gentle heating and agitation to provide a clear solution.

Example 4

2.00 g of Sodium Citrate Dihydrate (Aldrich) was dissolved in 20 g with water. pH was adjusted to 7.04 by addition of ~300 μL of sodium dihydrogencitrate (Aldrich Chemicals) which was 10% in water. 1.00 g of Irgacure®-2959 was mixed with 13.11 g of the citrate buffer, and then diluted to 100 g with water. The mixture was dissolved with gentle heating and agitation to provide a clear solution.

Example 5

2.00 g of sorbitol (Aldrich Chemicals) was dissolved in 20 g with water. 1.00 g of Irgacure®-2959 was mixed with 8.12 g of the sorbitol solution, and then diluted to 100 g with water. The mixture was dissolved with gentle heating and agitation to provide a clear solution.

Example 6

1.875 g of 4-hydroxy-2,2,6,6-tetramethylpiperidinyloxy, free radical (hereafter, 4-hydroxy-TEMPO) was dissolved in 25 mL of water.

Example 7

1.00 g of Irgacure 2959 (Ciba Specialty Chemicals) was dissolved in 99.00 g of water.

Example 8

10.00 g of polymer from Example 2 was mixed with 0.7425 of the solution from Example 7 and diluted to 12.00 g with water to afford a PEG/Irgacure® mixture at a ratio of 100:0.15.

Example 9

10.00 of polymer from Example 2 was mixed with 1.8960 g of the solution from Example 7 and diluted to 12.00 g with water to afford a PEG/Irgacure® mixture.

Example 10

10.00 g of polymer from Example 2 was mixed with 1.8960 g of the solution from Example 3 and diluted to 12.00 g with water to afford a PEG/Irgacure® mixture containing ascorbate.

Example 11

10.00 g of polymer from Example 2 was mixed with 1.8960 g of the solution from Example 4 and diluted to 12.00 g with water to afford a PEG/Irgacure® mixture containing citrate.

Example 12

10.00 g of polymer from Example 2 was mixed with 1.8960 g of the solution from Example 5 and diluted to 12.00 g with water to afford a PEG/Irgacure® mixture containing sorbitol.

Example 13

10.00 g of polymer from Example 2 was mixed with 1.8960 g of the solution from Example 6 and diluted to 12.00 g with water to afford a PEG/Irgacure® mixture containing 4-hydroxy-TEMPO.

Example 14

10.00 g of polymer from Example 1 was mixed with 0.7425 of the solution from Example 7 and diluted to 12.00 g with water to afford a PEG-Urea/Irgacure® mixture at a ratio of 100:0.15.

Example 15

10.00 g of polymer from Example 1 was mixed with 1.8960 g of the solution from Example 7 and diluted to 12.00 g with water to afford a PEG-Urea/Irgacure® mixture.

Example 16

10.00 g of polymer from Example 1 was mixed with 1.8960 g of the solution from Example 3 and diluted to 12.00 g with water to afford a PEG-Urea/Irgacure® mixture containing ascorbate.

Example 17

10.00 g of polymer from Example 1 was mixed with 1.8960 g of the solution from Example 4 and diluted to 12.00 g with water to afford a PEG-Urea/Irgacure® mixture containing citrate.

Example 18

10.00 g of polymer from Example 1 was mixed with 1.8960 g of the solution from Example 5 and diluted to 12.00 g with water to afford a PEG-Urea/Irgacure® mixture containing sorbitol.

Example 19

10.00 g of polymer from Example 1 was mixed with 1.8960 g of the solution from Example 6 and diluted to 12.00 g with water to afford a PEG-Urea/Irgacure® mixture containing 4-hydroxy-TEMPO.

Each of the above parent samples from Examples 8-19 were then divided into four. Samples with the above example numbers with no suffix (e.g., Example-11) were simply held under refrigeration. Samples with the above lot numbers suffixed with "T" (e.g., Example-11-T) were autoclaved in the dark at 121° C./30 minutes. Samples with the above lot numbers suffixed with "P" (e.g., Example-11-P) were subjected to 25 minute exposure to UV light. Samples of the above lot numbers suffixed with "PA" (e.g., Example-11-PA) were subjected to 25 minute exposure to UV light, followed by autoclave at 121° C./30 minutes.

UV light exposure was accomplished using a Macam Lamp with a Phillips HPA 400/30 S Sunlamp bulb. The output of the lamp was captured by an EFOS® Liquid Light Guide and focused on a cylindrical cell quartz cuvette available from Aldrich Chemicals as part number Z27696-0. The cuvette was filled with test substance and placed atop an assembly directly under the liquid light guide. Lamp intensity was ca. 1.8 mW/cm$^2$, and exposure time was 25 minutes, implying exposure dose of 2.7 J/cm$^2$.

The above-described samples were analyzed by Ion-Exchange Chromatography. The column used was an ICSep ICE-ORH-801 (0.65×300 mm) Transgenomic, P/N ICE-99-9754. The mobile phase was 10 mN $H_2SO_4$ at a flow rate of 0.8 mL/min. UV detection (λ=205 nm) was used to quantitate formic acid and total unknowns; Refractive Index detection was used to quantitate formaldehyde (sensitivity=512 mv). Injection volume was 100 µL and run time was 240 minutes.

degradation, formaldehyde, was present in PEG materials of Examples 8-13, whereas formaldehyde was not detected in

TABLE 1

| Sample | Polymer | Amendment | Treatment | HCOOH | HC(O)H | IC | Unknowns |
|---|---|---|---|---|---|---|---|
| Example 8 | PEG-2000 | 0.15% Initiator | Nitrogen | | 300 | 1579 | 3387845 |
| Example 8 P | PEG-2000 | | LS-1 UV | | 284 | 226 | 4089917 |
| Example 8 T | PEG-2000 | | Autoclaved | 56 | 247 | 1460 | 1600472 |
| Example 8 PA | PEG-2000 | | autoclaved + LS-1 UV | 319 | 165 | 234 | 3387845 |
| Example 9 | PEG-2000 | 0.38% Initiator | Nitrogen | ND | 276 | 4019 | 1561001 |
| Example 9 P | PEG-2000 | | LS-1 UV | ND | 308 | 466 | 9413559 |
| Example 9 T | PEG-2000 | | Autoclaved | 156 | 272 | 3786 | 1625876 |
| Example 9 PA | PEG-2000 | | autoclaved + LS-1 UV | 219 | 217 | 442 | 8508847 |
| Example 10 | PEG-2000 | Ascorbate Buffer | Nitrogen | | 291 | 4146 | 1759608 |
| Example 10 P | PEG-2000 | | LS-1 UV | | 337 | 136 | 21333767 |
| Example 10 T | PEG-2000 | | Autoclaved | 51 | 301 | 3822 | 1451887 |
| Example 10 PA | PEG-2000 | | autoclaved + LS-1 UV | | 250 | 380 | 19728127 |
| Example 11 | PEG-2000 | Citrate Buffer | Nitrogen | | 317 | 3825 | 1799368 |
| Example 11 P | PEG-2000 | | LS-1 UV | | 339 | 482 | 8699143 |
| Example 11 T | PEG-2000 | | Autoclaved | | 339 | 3747 | 1425557 |
| Example 11 PA | PEG-2000 | | autoclaved + LS-1 UV | | 290 | 554 | 8110747 |
| Example 12 | PEG-2000 | Sorbitol | Nitrogen | | 299 | 3967 | 1679516 |
| Example 12 P | PEG-2000 | | LS-1 UV | | 243 | 375 | 7442590 |
| Example 12 T | PEG-2000 | | Autoclaved | 188 | 228 | 3723 | 1421715 |
| Example 12 PA | PEG-2000 | | autoclaved + LS-1 UV | 240 | 193 | 432 | 7803607 |
| Example 13 | PEG-2000 | TEMPO | Nitrogen | | 286 | 3586 | 1715501 |
| Example 13 P | PEG-2000 | | LS-1 UV | | 306 | 466 | 9072232 |
| Example 13 T | PEG-2000 | | Autoclaved | | 302 | 2885 | 1155402 |
| Example 13 PA | PEG-2000 | | autoclaved + LS-1 UV | 156 | 266 | 692 | 9481513 |

IC stands for Irgacure ® initiator.

Table 1 shows results of ion-exchange chromatography of samples generated in Examples 11-16. All results expressed in parts-per-million (µg/mL). A blank entry means that the analyte concentration was below the detection limit (50 ppm for formic acid)

any PEG-urea polymers in Examples 14-19 (Table 2). The nature of the amendment added to the formulation had dramatic effects on by-product generation during the curing/autoclaving steps. As can be seen, sorbitol, whose hydroxyl groups should act as chain transfer agents, had very little

TABLE 2

| Sample | Polymer | Amendment | Treatment | HCOOH | HC(O)H | Irgacure | Unknowns |
|---|---|---|---|---|---|---|---|
| Example 14 | PEG-Urea | 0.15% Irgacure | Nitrogen | | | 989 | 626725 |
| Example 14 P | PEG-Urea | | LS-1 UV | 78 | | 202 | 1205303 |
| Example 14 T | PEG-Urea | | Autoclaved | | | 1364 | 1021780 |
| Example 14 PA | PEG-Urea | | autoclaved + LS-1 UV | 195 | | 243 | 869404 |
| Example 15 | PEG-Urea | 0.38% Irgacure | Nitrogen | | | 2842 | 448187 |
| Example 15 P | PEG-Urea | | LS-1 UV | | | 533 | 7932312 |
| Example 15 T | PEG-Urea | | Autoclaved | | | 4690 | 475180 |
| Example 15 PA | PEG-Urea | | autoclaved + LS-1 UV | 136 | | 868 | 7232686 |
| Example 16 | PEG-Urea | Ascorbate Buffer | Nitrogen | | | 3593 | 697009 |
| Example 16 P | PEG-Urea | | LS-1 UV | 69 | | 165 | 21371459 |
| Example 16 T | PEG-Urea | | Autoclaved | | | 4235 | 799883 |
| Example 16 PA | PEG-Urea | | autoclaved + LS-1 UV | 60 | | 380 | 16135664 |
| Example 17 | PEG-Urea | Citrate Buffer | Nitrogen | | | 3170 | 535949 |
| Example 17 P | PEG-Urea | | LS-1 UV | | | 662 | 7178992 |
| Example 17 T | PEG-Urea | | Autoclaved | | | 3919 | 669291 |
| Example 17 PA | PEG-Urea | | autoclaved + LS-1 UV | 74 | | 521 | 5752951 |
| Example 18 | PEG-Urea | Sorbitol | Nitrogen | | | 3238 | 614870 |
| Example 18 P | PEG-Urea | | LS-1 UV | | | 746 | 7979709 |
| Example 18 T | PEG-Urea | | Autoclaved | | | 4499 | 629794 |
| Example 18 PA | PEG-Urea | | autoclaved + LS-1 UV | 124 | | 551 | 5327765 |
| Example 19 | PEG-Urea | TEMPO | Nitrogen | | | 3178 | 499934 |
| Example 19 P | PEG-Urea | | LS-1 UV | | | 439 | 4215228 |
| Example 19 T | PEG-Urea | | Autoclaved | | | 5232 | 504369 |
| Example 19 PA | PEG-Urea | | autoclaved + LS-1 UV | 104 | | 595 | 5215616 |

Table 2 shows results of ion-exchange chromatography of samples generated in Examples 14-19. All results expressed in parts-per-million (µg/mL). A blank entry means that the analyte concentration was below the detection limit.

As can be seen from the tables, the levels of formic acid in the irradiated and autoclaved samples were highest for any given family of samples. Furthermore, a second by-product of efficacy as a stabilizer. The free-radical scavenger TEMPO had a modest effect on lowering the amount of detectable by-products, reducing them by approximately 25%. But the ascorbate and citrate buffered formulations had little or no detectable formic acid in any of the samples, indicating a large stabilizing effect brought by these materials. The efficacy of these two stabilizers versus the more conventional stabilizers sorbitol and TEMPO was unexpected.

There is a difference between the two buffers in terms of side effects. This was conveniently quantified by monitoring the "total unknowns" in the chromatograms. These unknowns have been partially characterized in that they are known to represent Irgacure decomposition products, high-molecular weight fragments of degraded polymer, and the like. In general, non-irradiated samples had total unknowns on the order of $2 \times 10^6$ counts; on irradiation, the unknowns increased to about $9 \times 10^6$ counts. Citrate-buffered PEG followed this trend with $1.8 \times 10^6$ counts before irradiation and $8.7 \times 10^6$ counts after irradiation and autoclave. Ascorbate buffered polyethylene glycol, however, showed an unknowns level of $1.8 \times 10^6$ counts before irradiation and $21.3 \times 10^6$ counts after, a ten-fold increase. All of the trends observed for the PEG were observed for the PEG Urea. There was thus a large and unexpected stabilization of PEG and PEG-Urea in the presence of an organic multi-acid of the present invention.

Example 20

2.45 g of Pyruvic Acid Sodium Salt (Aldrich) were diluted to 100 g with water. The pH of this solution was adjusted to 7.2 by addition of 15% aqueous sodium hydroxide. 0.5 g of Irgacure®-2959 was dissolved in 49.5 g of this mixture. 5.00 g of polymer from Example 1 was mixed with 0.75 g of this initiator solution and diluted to 6.00 g with water to afford a PEG-Urea/Irgacure® mixture containing pyruvate.

Example 21

3.75 g of 2-Ketoglutaric Acid Monosodium Salt (Aldrich) were diluted to 100 g with water. The pH of this solution was adjusted to 7.2 by addition of 15% aqueous sodium hydroxide. 0.5 g of Irgacure®-2959 was dissolved in 49.5 g of this mixture. 5.00 g of polymer from Example 1 was mixed with 0.75 g of this initiator solution and diluted to 6.00 g with water to afford a PEG-Urea/Irgacure® mixture containing 2-ketoglutarate.

Example 22

2.99 g of Malic Acid (Aldrich) were diluted to 100 g with water. 2.99 g of Malic Acid Disodium Salt (Aldrich) were diluted to 100 g with water. The pH of this Malic Acid Disodium Salt solution was adjusted to 7.2 by addition of a small amount of the Malic Acid solution. 0.5 g of Irgacure®-2959 was dissolved in 49.5 g of this mixture. 5.00 g of polymer from Example 1 was mixed with 0.75 g of this initiator solution and diluted to 6.00 g with water to afford a PEG-Urea/Irgacure® mixture containing malate buffer.

Samples of the above Examples 20, 21, and 22 were subjected to 25-minute exposure to UV light, followed by autoclave at 121° C./30 minutes. UV light exposure was accomplished using a Macam Lamp with a Phillips HPA 400/30 S Sunlamp bulb directed by an EFOS® Liquid Light Guide and focused on a cylindrical cell quartz cuvette as described above. Lamp intensity was ca. 1.8 mW/cm², and exposure time was 25 minutes, implying exposure dose of 2.7 J/cm².

The samples were subjected to Ion Exchange Chromatography with the following results:

| Sample | Treatment | HCOOH | HC(O)H | Irgacure | Unknowns |
|---|---|---|---|---|---|
| Example 20 | Pyruvate | 200 | | 115 | 4481172 |
| Example 21 | Ketoglutarate | | | 286 | 2567220 |
| Example 22 | Malate | | | 187 | 713127 |

A blank entry in the above table means that the analyte concentration was below detection limits. It can thus be seen from the above examples that α-oxo-diacids have unexpected, beneficial results in regard to PEG stabilization which are not realized in the case of the an α-oxo monoacid.

Example 23

74.26 g of Jeffamine XTJ-501 (from Huntsman Corporation), and 3.1 g of diethylene triamine (Aldrich Chemicals) were weighed into a jacketed 1-L reactor. 450 g of tetrahydrofuran (Aldrich) and 250 g of deionized water were added to the reactor and the contents were stirred to dissolve. The reactor was then chilled to 0° C. with stirring under nitrogen. 23.34 g of isophorone diisocyanate (Aldrich Chemicals, used as received) was then dissolved in 50 g of THF and added dropwise over 45 minutes. The solution was stirred at temperature for one. 20 g of 20% aqueous Sodium Carbonate (Aldrich) were added to the reactor and stirred to mix. 2.8 g of acryloyl chloride (Aldrich Chemicals, used as received) was then added in one portion, and the reactor was stirred at 0° C. for 30 minutes. Treatment of the reaction mixture with 20 g 20% sodium carbonate, followed by 2.8 g of acryloyl chloride, was repeated twice more at 30 minute intervals. The product was then decanted to a 2-L flask, and the reactor was chased with 400 mL of water. The mixture was filtered with a 40 μm sintered glass filter. The product was then concentrated on a rotary evaporator at 53° C./80 mBar ultimate vacuum to yield a solution essentially free of tetrahydrofuran. This solution was then ultrafiltered with 10 L of water using a 1-kilodalton membrane. The resulting purified solution was then concentrated to 25.33% solids on a rotary evaporator.

Example 24

11.76 g of Sodium Citrate Dihydrate (Aldrich) was diluted to 1.0 L with water in a volumetric flask. 0.8564 g of Sodium Dihydrogencitrate (Aldrich) was diluted to 100 mL with water in a 100 mL volumetric. Both solutions were thus 40 mM of citrate. The Sodium Citrate Dihydrate solution was pH-adjusted to 7.2 by adding the Sodium Dihydrogencitrate solution. 8.2 g of sodium chloride was then weighed into a 1-L volumetric and diluted to the mark with the citrate buffer.

Example 25

4.76 g of Disodium Phosphate (Aldrich), 0.77 g of Sodium Phosphate (Aldrich), and 8.2 g of sodium chloride were weighed into a 1-L volumetric and diluted to the mark with water.

Example 26

47.37 g of the 25.33% solids solution of Example 23 were weighed into a rotary evaporator flask. 19.77 g of water were removed at 55° C./70-100 mBar. 2.4 g of initiator solution from Example 7 were added and the mixture was agitated to homogenize.

Example 27

44 mg of the material afforded by Example 26 was dosed into a quartz mold and the mold was closed. The mold was then exposed to UV light using a Macam Lamp with a Phillips HPA 400/30 S Sunlamp bulb. The output of the lamp was captured by an EFOS® Liquid Light Guide and focused into the mold. The intensity of the lamp was 1.85 mW/cm² and the exposure time was 20 s, implying an exposure energy of 37 mJ/cm². The molds were opened and the resulting contact lens was rinsed off. Five lenses made in this way were placed in autoclave vials which contained 2.5 mL of the buffered saline of Example 24. The lenses were then subjected to 5 autoclave cycles (121° C./30 minutes). The salines were then combined and analyzed by ion-exclusion chromatography. The saline was found to have 9 ppm of formic acid, a value below the Occupational Safety and Health Administration's Short-Term Exposure Limit (STEL) of 10 ppm.

Example 28

44 mg of the material afforded by Example 26 was dosed into a quartz mold and the mold was closed. The mold was then exposed to UV light using a Macam Lamp with a Phillips HPA 400/30 S Sunlamp bulb. The output of the lamp was captured by an EFOS® Liquid Light Guide and focused into the mold. The intensity of the lamp was 1.85 mW/cm² and the exposure time was 20 s, implying an exposure energy of 37 mJ/cm². The molds were opened and the resulting contact lens was rinsed off.

Five lenses made in this way were placed in autoclave vials which contained 2.5 mL of the buffered saline of Example 25. The lenses were then subjected to 5 autoclave cycles (121° C./30 minutes). The salines were then combined and analyzed by ion-exclusion chromatography. The saline was found to have 36 ppm of formic acid. This value is well above the Occupational Safety and Health Administration's Short-Term Exposure Limit (STEL) of 10 ppm, rendering the lenses unfit for use.

The utility of the organic multi-acids of the present invention was thus unexpectedly equivalent regardless of where in the processing the organic multi-acids is employed.

Example 29

Preparation of Acrylamide-Capped Polyurea

Place 2017 grams of tetrahydrofuran (THF), 1257 grams of water, 420 amine group milliequilvalents (meq) of Jeffamine® XTJ501 (Hunstman Chemicals), 250 amine group meq of Jeffamines® XTJ502 (Hunstman Chemicals), 134 amine group meq of bis-hexamethylenetriamine (Aldrich Chemicals) into a jacketed 5L reactor. At a temperature of approximately from 0 to 5° C., add a solution of 500 isocyanate group meq of isophorone diisocyanate (Aldrich Chemicals), 134 isocyanate group meq of VESTANAT® T1890/100 (Degussa Chemicals) and about 370 grams of THF drop wise with intensive stirring over about 30 minutes. Keep the solution temperature at approximately 0 to 5° C. for approximately 25 minutes. Add approximately 108 grams of a 20% sodium carbonate aqueous solution, followed by 17 grams of acryloyl chloride (Aldrich Chemicals) to the solution. After 30 minutes, add a second aliquot of 108 grams of sodium carbonate solution followed by 17 grams of acryloyl chloride. Discontinue cooling after the second addition. After 30 minutes, add a third aliquot of 108 grams of sodium carbonate solution followed by 3.4 grams of acryloyl chloride. Thirty minutes after the final addition, drain the reaction mixture from the reactor, then rinse the reactor with a small amount of THF or water. Filter the mixture through a 17 μm sintered glass filter under vacuum. Concentrate the solution under vacuum using a rotary evaporator to yield a solution essentially free of THF. Ultrafilter this solution with approximately 31 L of water using a 1-kilodalton membrane. Further purify the solution by passing the solution through a 0.45 μm Teflon membrane under pressure. Stabilize the macromer solution with 50 ppm of hydroxyl-TEMPO (versus the polymer). Concentrate the solution to approximately 49% solids under vacuum using a rotary evaporator.

Example 30

Dissolve 1.875 g of 4-hydroxy-2,2,6,6-tetramethylpiperidinyloxy, free radical (hereafter, 4-hydroxy-TEMPO) in 25 mL of water.

Example 31

Preparation of Formulation. Mix 19.47 grams of the polymer solution from Example 29 (49.3% polymer), 0.0576 grams of the solution from Example 30, 1.92 grams of the solution from Example 7, 7.67 grams of D.I. water, and 1.58 grams of visitint solution. Place the formulation containing 32% polymer, 80 ppm of 4-hydroxy-TEMPO, 0.2% Irgacure and 42 ppm of visitint into 5 mL syringes and centrifuge for 15 minutes at 4500 rpm.

Example 32

Preparation of Formulation containing CBS. Mix 6.49 grams of the polymer solution from Example 29, 0.0192 grams of the solution from Example 30, 0.64 grams of the solution from Example 7, 2.69 grams of 60 mM CBS described in Example 37, and 0.158 grams of visitint solution. Place the formulation containing 32% polymer, 80 ppm of 4-hydroxy-TEMPO, 0.2% Irgacure, 16 mM of CBS, and 42 ppm of visitint into 5 mL syringes and centrifuge for 15 minutes at 4500 rpm.

Example 33

Preparation of Contact Lenses. Place about 2 drops of the formulation from Example 31 (or Example 32) into a quartz mold (−1.0 diopters). Irradiate the formulation with 17 mJ of energy using the Macam lamp described in Examples 19. Place the resulting lenses into 0.85 mL of various buffer solutions. Use fifteen lenses for each buffer solution. Autoclave five lenses with buffer solution once, five lenses 3 times and five lenses 5 times. Each autoclave cycle is 121° C. for 30 minutes.

Example 34

Preparation of 20 mM Citrate Buffered Saline CBS. Weigh 5.88 grams of sodium citrate dihydrate (Aldrich Chemicals), 0.060 grams of Sodium Dihydrogencitrate (Aldrich), and 7.70 grams of sodium chloride into a 1-L volumetric flask and dilute to the mark with D.I. water. The pH of the solution is 7.05 and the osmolarity is 300 mOsm.

Example 35

Preparation of 40 mM Citrate Buffered Saline CBS. Weigh 11.76 grams of sodium citrate dihydrate (Aldrich Chemicals), 0.121 grams of Sodium Dihydrogencitrate (Aldrich), and 5.90 grams of sodium chloride into a 1-L volumetric flask and dilute to the mark with D.I. water. The pH of the solution is 7.08 and the osmolarity is 302 mOsm.

Example 36

Preparation of 40 mM Citrate Buffered Saline CBS at low pH. Weigh 0.420 grams of citric acid monohydrate (Aldrich Chemicals), 0.428 grams of Sodium Dihydrogencitrate (Aldrich), and 0.70 grams of sodium chloride into a 100 mL volumetric flask and dilute to the mark with D.I. water. The pH of the solution is 3.67 and the osmolarity is 292 mOsm.

Example 37

Preparation of 60 mM Citrate Buffered Saline CBS. Weigh 17.64 grams of sodium citrate dihydrate (Aldrich Chemicals), 0.182 grams of Sodium Dihydrogencitrate (Aldrich), and 4.20 grams of sodium chloride into a 1-L volumetric flask and dilute to the mark with D.I. water. The pH of the solution is 7.10 and the osmolarity is 306 mOsm.

Example 38

Measurement of formic acid concentration. Combine the buffer solution of 2 lenses from each condition and test for formic acid using the method described in Example 18. Table 4 lists the average amount of formic acid in ppm from 2 different samples. The detection limit of the instrument is 0.3 ppm

| Number of autoclave cycles | 20 mM CBS | 40 mM CBS with low pH | 40 mM CBS | 40 mM w/CBS in formulation | 60 mM CBS | 40 mM PBS | water | 40 mM CBS with no lens |
|---|---|---|---|---|---|---|---|---|
| 1 | <0.3 | <0.3 | <0.3 | 0.6 | <0.3 | 4.7 | 7.0 | <0.3 |
| 3 | 1.1 | 3.5 | 2.9 | 8.8 | 6.8 | 135 | 17.0 | 0.6 |
| 5 | 5.0 | 5.0 | 8.4 | 14.8 | 14.3 | 191 | 106.0 | 3.6 |

The addition of citrate buffered saline at all concentrations used reduces the amount of formic acid formed by the lenses versus water and PBS. The effect is most obvious at 5 autoclave cycles where the formic acid concentration is more than an order of magnitude higher in water or PBS than in 40 mM CBS. CBS also functions to reduce the formation of formic acid during the at low pH (3.67) using similar conditions. CBS concentrations of 20, 40 and 60 mM are all acceptable. Having CBS in the formulation during the UV cure does not further reduce the concentration of formic acid after 5 autoclave cycles versus 60 mM CBS.

Although various embodiments of the invention have been described using specific terms, devices, and methods, such description is for illustrative purposes only. The words used are words of description rather than of limitation. It is to be understood that changes and variations may be made by those skilled in the art without departing from the spirit or scope of the present invention, which is set forth in the following claims. In addition, it should be understood that aspects of the various embodiments may be interchanged either in whole or in part. Therefore, the spirit and scope of the appended claims should not be limited to the description of the preferred versions contained therein.

What is claimed is:

1. A method for sterilizing a medical device having a core material and/or a coating, wherein the core material and the coating, independently of each other, are made of a poly (oxyalkylene)-containing polymeric material, the method comprising: autoclaving the medical device in a solution containing from 10 to 300 millimolar of citric acid or biocompatible salt thereof while decreasing susceptibility to oxidative degradation of the poly(oxyalkylene)-containing polymeric material as characterized by having at least an 1.5-fold reduction of the amount of detectable formic acid and optionally other degradation by-products derived from oxidative degradation of the poly(oxyalkylene)-containing polymeric material relative to that for the poly(oxyalkylene)-containing polymeric material without citric acid or biocompatible salt thereof, wherein the biocompatible salt of citric acid is a sodium, potassium, or ammonium salt.

2. The method of claim 1, wherein the citric acid or biocompatible salt thereof is present in an amount from 20 milimolar to 60 milimolar.

3. The method of claim 1, wherein the solution has an osmolarity of from about 200 to 450 milli-osmole in 1000 ml (unit: mOsm/ml).

4. The method of claim 2, wherein the solution has an osmolarity of from about 200 to 450 milli-osmole in 1000 ml (unit: mOsm/ml).

* * * * *